United States Patent
Boden et al.

(10) Patent No.: US 10,188,535 B2
(45) Date of Patent: Jan. 29, 2019

(54) MEDICAL DEVICES HAVING ENHANCED PERFORMANCE

(71) Applicant: Boston Scientific Scimed, Inc., Maple Grove, MN (US)

(72) Inventors: Mark Boden, Harrisville, RI (US); Patrick Mather, Oxford, PA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 19 days.

(21) Appl. No.: 14/936,251

(22) Filed: Nov. 9, 2015

(65) Prior Publication Data

US 2016/0129159 A1    May 12, 2016

Related U.S. Application Data

(60) Provisional application No. 62/076,865, filed on Nov. 7, 2014.

(51) Int. Cl.
| | |
|---|---|
| *A61F 2/82* | (2013.01) |
| *A61F 2/915* | (2013.01) |
| *A61L 31/12* | (2006.01) |
| *A61F 2/958* | (2013.01) |

(52) U.S. Cl.
CPC .......... *A61F 2/915* (2013.01); *A61L 31/129* (2013.01); *A61F 2/958* (2013.01); *A61F 2002/91558* (2013.01)

(58) Field of Classification Search
CPC ................ A61F 2/82; A61F 2/06; A61F 2/92
USPC ................................... 623/1.1–1.48
See application file for complete search history.

(56) References Cited

U.S. PATENT DOCUMENTS

| | | | |
|---|---|---|---|
| 2011/0144737 A1* | 6/2011 | Burgermeister | A61L 27/26 623/1.16 |
| 2015/0306282 A1* | 10/2015 | Scanlon | A61L 31/14 623/1.11 |
| 2016/0000592 A1* | 1/2016 | Huang | A61F 2/90 623/1.15 |
| 2017/0079813 A1* | 3/2017 | Bar | A61F 2/07 |
| 2017/0095358 A1* | 4/2017 | Savage | A61F 2/915 |

* cited by examiner

*Primary Examiner* — Suzette J Gherbi

(57) ABSTRACT

In some aspects, the present disclosure provides medical devices that comprise a composite region comprising a binding polymer portion and an oriented fibrous polymer reinforcement portion, wherein the composite region is formed by a process that comprises heating and compressing one or more oriented polymer fibers. Other aspects of the present disclosure relative to methods of forming such medical devices.

14 Claims, 2 Drawing Sheets

MEDICAL DEVICES HAVING ENHANCED PERFORMANCE

This application claims the benefit of U.S. Provisional Application Ser. No. 62/076,865, filed Nov. 7, 2014 and entitled "MEDICAL DEVICES HAVING ENHANCED PERFORMANCE", which is hereby incorporated by reference.

BACKGROUND

Stents, grafts, stent-grafts, vena cava filters, expandable frameworks and similar implantable medical devices are radially expandable endoprostheses, which are typically capable of being implanted transluminally and enlarged radially after being introduced into a body lumen.

Stents, for example, may be implanted in a variety of bodily lumens, including blood vessels within the vascular system (e.g., coronary vessels, secondary vessels, etc.), lumens of the urinary tract, bile ducts, fallopian tubes, and so forth. Stents are commonly either balloon-expandable or self-expanding, depending upon how deployment is carried out. Balloon-expandable stents are manufactured in a crimped state and expanded to vessel diameter by inflating a balloon and plastically deforming the stent. Self-expanding stents are manufactured at or somewhat above vessel diameter and are crimped and constrained to the smaller diameter until the intended delivery site is reached, where the constraint is removed and the stent deployed. Thus, self-expanding stents, instead of being plastically deformed to the vessel diameter, expand by simply reverting to an equilibrium shape.

Stents are commonly manufactured from either metal or polymer tubes, often by laser or chemical or mechanical machining. The stent mechanical properties are typically dependent upon the properties of the material from which they are formed. Stents made of metal typically have relatively high strength, stiffness, and radiopacity and less elastic recoil upon expansion relative to stents made of polymer. This is because metals tend to have a higher Young's modulus of elasticity, higher yield strength, higher work hardening rate, and higher density than polymers. Polymer stents typically have more axial and radial flexibility than metal stents with the same wall thickness due to the polymer's lower modulus of elasticity.

The mechanical properties of polymer stents, however, typically require significant compromises in design in order to close the gap in mechanical properties relative to metal stents. For example, in order to reach the radial strength and stiffness of metal stents, polymer stents commonly need to have a wall thickness that is significantly greater than the wall thickness of a comparable metal stent. This undesirably increases the profile of the polymer stent such that it occupies more of the vessel luminal area, thus reducing the volume of fluid flow in the stented lumen.

SUMMARY

In some aspects, the present disclosure provides medical devices that comprise a composite region comprising a binding polymer portion and an oriented fibrous polymer reinforcement portion.

In certain embodiments, the composite region is formed by a process that comprises heating and compressing one or more oriented polymer fibers (e.g., fibers formed from a process that comprises drawing spun polymer fibers, among other possible processes).

In certain embodiments, which may be used in combination with any of the above aspects and embodiments, the medical devices may be expandable medical devices that comprise an expandable framework, which expandable framework comprises the composite region.

In some embodiments, which may be used in combination with any of the above aspects and embodiments, the binding polymer portion is in the form of a polymer matrix that surrounds fibers of the oriented fibrous polymer reinforcement portion.

In some embodiments, which may be used in combination with any of the above aspects and embodiments, the oriented fibrous polymer reinforcement portion is crystalline, for example, having a crystallinity of at least 50% in certain instances.

In some embodiments, which may be used in combination with any of the above aspects and embodiments, the value of Herman's orientation function (f) for the composite may range between 0.25 and 0.9, for example, ranging from 0.25 to 0.30 to 0.35 to 0.40 to 0.50 to 0.60 to 0.70 to 0.80 to 0.90 (i.e., ranging between any two of the preceding numerical values), for instance, beneficially ranging from 0.5 to 0.9 in some embodiments, among other ranges.

In some embodiments, which may be used in combination with any of the above aspects and embodiments, the composite region is a self-reinforced composite region in which the binding polymer portion and the oriented fibrous polymer reinforcement portion are formed from one or more oriented polymer fibers having the same composition. For example, in some instances, the self-reinforced composite region may be formed by partial melting of the one or more oriented polymer fibers such that the binding polymer portion is formed from a melted outer portion of the one or more oriented polymer fibers and the oriented fibrous polymer reinforcement portion is formed from a residual core region of the one or more oriented polymer fibers.

In other embodiments, which may be used in combination with any of the above aspects and embodiments, the binding polymer portion is formed from a first polymer and the oriented fibrous polymer reinforcement portion is formed from a second polymer that is different than the first polymer. For example, the composite region may be formed by compressing and heating one or more first polymer fibers formed from the first polymer and one or more second oriented polymer fibers formed from the second polymer, under conditions such that the compressing and heating is sufficient to cause the first polymer to flow and form the binding polymer portion while at the same time preserving the one or more second oriented polymer fibers in a fiber form that corresponds to the oriented fibrous polymer reinforcement portion. As another example, the composite region may be formed by compressing and heating one or more polymer fibers that comprise an oriented polymer core formed from the second polymer and a polymer coating formed from the first polymer, under conditions such that the compressing and heating is sufficient to cause the coating to flow and form the binding polymer portion while at the same time preserving the polymer core in a fiber form that corresponds to the oriented fibrous polymer reinforcement portion.

In certain embodiments, which may be used in combination with any of the above aspects and embodiments, the oriented fibrous polymer reinforcement portion may comprise polylactide. For example, the oriented fibrous polymer reinforcement portion may comprise polylactide and the binding polymer portion may comprise polylactide. As another example, the oriented fibrous polymer reinforcement portion may comprise polylactide and the binding polymer portion may comprise poly(lactide-co-glycolide). For instance, the composite region may be formed by a process that comprises heating and compressing one or more fibers that comprise an oriented polylactide core and a poly(lactide-co-glycolide) coating, or the composite region may be formed by a process that comprises heating and compressing a mixture of fibers that comprises polylactide fibers and poly(lactide-co-glycolide) fibers.

In certain beneficial embodiments, which may be used in combination with any of the above aspects and embodiments, the medical device may be a stent and the expandable framework may be a stent body, and wherein the stent body comprises a plurality of stent struts.

In these embodiments, the oriented fibrous polymer reinforcement portion may comprise one of the following, any two of the following (e.g., (a) in combination with (b), etc.), or all three of the following: (a) a first fraction of the oriented fibrous polymer reinforcement portion oriented at a first angle ranging from 20° to 70°, for example ranging from 20° to 30° to 40° to 50° to 60° to 70°, relative to an imaginary line lying at a surface of the stent body that is parallel to the longitudinal axis of the stent body, for instance, beneficially ranging from 30° to 60° relative to the imaginary line in some embodiments, among other ranges, where the stent struts comprise first strut segments aligned with the first fraction, when the stent is in an expanded or crimped state, (b) a second fraction of the oriented fibrous polymer reinforcement portion oriented at a second angle ranging from −20° to −70°, for example ranging from −20° to −30° to −40° to −50° to −60° to −70°, relative to the imaginary line, for instance, beneficially ranging from −30° to −600 relative to the imaginary line in some embodiments, among other ranges, and wherein the stent struts comprise second strut segments aligned with the second fraction, when the stent is in an expanded or crimped state, and (c) a third fraction of the oriented fibrous polymer reinforcement portion oriented at a third angle ranging from 70°-120°, for example, ranging from 70° to 80° to 85° to 88° to 90° to 92° to 95° to 100° to 110° to 120°, relative to the imaginary line, for instance, beneficially ranging from 85° to 95° relative to the imaginary line in some embodiments, among other ranges, and wherein the stent struts comprise third strut segments aligned with the third fraction, when the stent is in an expanded or crimped state. In some instances, the stent may be disposed on a balloon, with the preceding conditions being met when the balloon is in a fully expanded state.

In some aspects, the present disclosure provides an assembly comprising a balloon and a stent disposed on the balloon, wherein the stent comprises an expandable stent body that comprises a composite region comprising a binding polymer portion and an oriented fibrous polymer reinforcement portion, wherein the composite region is formed by a process that comprises heating and compressing one or more oriented polymer fibers. The stent body comprises a plurality of stent struts. Upon expansion of the stent by the balloon, the oriented fibrous polymer reinforcement portion comprises one of the following fractions, any two of the following fractions, or all three of the following fractions: (a) a first fraction of the oriented fibrous polymer reinforcement portion oriented at a first angle ranging from 20° to 70°, for instance, 30° to 60°, relative to an imaginary line lying at a surface of the stent body that is parallel to the longitudinal axis of the stent body, wherein the stent struts comprise first strut segments aligned with the first fraction, (b) a second fraction of the oriented fibrous polymer reinforcement portion oriented at a second angle ranging from −20° to −70°, for instance, −30° to −60°, relative to the imaginary line, wherein the stent struts comprise second strut segments aligned with the second fraction, and (c) a third fraction of the oriented fibrous polymer reinforcement portion oriented at a third angle ranging from 70° to 120°, for instance, 85° to 95°, relative to the imaginary line, and wherein the stent struts comprise third strut segments aligned with the third fraction.

In some aspects, the present disclosure provides methods of making medical devices that comprise a composite region, the method comprising (a) forming a cylindrical structure by winding at least one polymer fiber comprising at least one oriented polymer fiber around a mandrel and (b) heating and compressing the at least one polymer fiber under conditions such that a composite cylindrical structure is formed, the composite cylindrical structure comprising a binding polymer portion and an oriented fibrous polymer reinforcement portion.

In some embodiments, the methods may be used to form expandable medical devices that comprise an expandable framework formed from the composite cylindrical structure.

In some embodiments, which may be used in combination with the above aspects and embodiments, the at least one polymer fiber is wound on a rotating mandrel and the at least one polymer fiber is fed from a reciprocating carriage. In some of these embodiments, the at least one polymer fiber is heated and compressed by pressing a heated roller against the at least one polymer fiber on the rotating mandrel.

In some embodiments, which may be used in combination with the above aspects and embodiments, the at least one polymer fiber is heated and compressed by first compressing the at least one polymer fiber and subsequently applying heat to the at least one polymer fiber.

In some embodiments, which may be used in combination with the above aspects and embodiments, medical device may be a stent that comprises a plurality of stent struts that may be formed from the composite cylindrical structure. For example, the composite cylindrical structure may be cut to form the stent struts, among other methods.

In some embodiments, which may be used in combination with the above aspects and embodiments, the method comprises comprising winding the at least one polymer fiber at one of the following winding angles, any two of the following winding angles, or all three of the following winding angles: (a) winding at least a portion of the at least one polymer fiber at a first winding angle ranging from 20° to 70°, for example ranging from 20° to 30° to 40° to 50° to 60° to 70°, relative to an imaginary line lying at a surface of the mandrel that is parallel to the longitudinal axis of the mandrel, for instance, beneficially ranging from 30° to 60° relative to the imaginary line in some embodiments, among other ranges, (b) winding at least a portion of the at least one polymer fiber at a second winding angle ranging from −20° to −70°, for example ranging from −20° to −30° to −40° to −50° to −60° to −70°, relative to the imaginary line, for instance, beneficially ranging from −30° to −60° relative to the imaginary line in some embodiments, among other ranges, and (c) winding at least a portion of the at least one polymer fiber at a third winding angle ranging from 70°-120°, for example, ranging from 70° to 80° to 85° to 88° to 90° to 92° to 95° to 100° to 110° to 120°, relative to the imaginary line, for instance, beneficially ranging from 85° to 95° relative to the imaginary line in some embodiments, among other ranges. In these embodiments, the medical device formed may be a stent having a plurality of stent struts that comprise one of the following strut segments, any two of the following strut segments, or all three of the following strut segments: (a) first strut segments aligned with the first winding angle, (b) second strut segments aligned with the second winding angle, and (c) third strut segments aligned with the third winding angle.

These and other aspects, embodiments and advantages of the present disclosure will become immediately apparent to those of ordinary skill in the art upon review of the detailed description and claims to follow.

DETAILED DESCRIPTION

Figure 1:
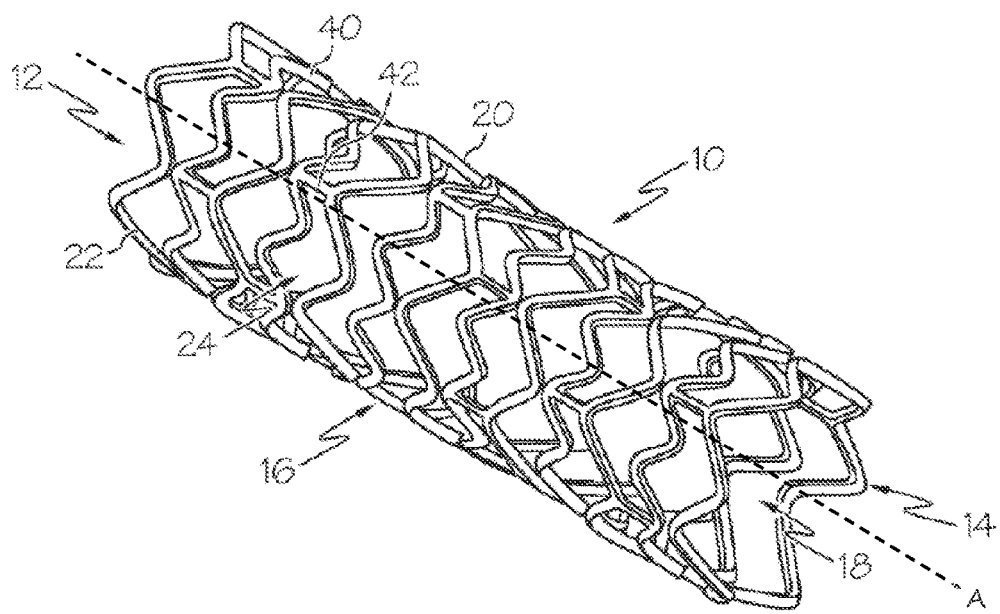
FIG. 1 is a schematic illustration of an enhanced strength polymer stent in accordance with one embodiment of the present disclosure.

The present disclosure is directed to medical devices, including medical devices having radially expandable polymer frameworks. Such devices are typically capable of being implanted transluminally and enlarged radially after being introduced into a body lumen. Medical devices formed in accordance with the present disclosure include balloon expandable structures (which may optionally be delivered using a heated balloon) and self-expanding structures.

It should be noted that, although the detailed description of the present disclosure generally exemplifies radially expandable devices such as stents, the present disclosure is not so limited, and pertains to a wide variety of medical devices. Specific examples of medical devices which may be provided in accordance with the present disclosure include, for example, stent-grafts, vena cava filters, hernia meshes, meshes for pelvic floor repair, venous valves, and artificial heart valves, among others.

As noted above, polymeric stents have generally been found to be mechanically inferior to metallic stents. It is also true, on the other hand, that polymeric fibers are among the highest stiffness materials known to man. In the present disclosure, oriented polymeric fibers are used to yield high performance expandable polymer frameworks, including stents of sufficient radial strength and stiffness to allow for the creation of strut thicknesses and widths approaching those of metallic stents.

Stents formed in accordance with the present disclosure are adapted for deployment at various placement sites within the patient, and include vascular stents (e.g., coronary stents and peripheral vascular stents such as cerebral stents), urinary stents (e.g., urethral stents and ureteral stents), biliary stents, fallopian stents, bronchotracheal stents, and gastrointestinal stents including esophageal stents.

A specific example of a stent in accordance with the present disclosure will now be discussed in conjunction with FIG. 1, which shows an embodiment of an enhanced strength polymer stent in an expanded state, and FIG. 2, which shows an enlarged view of an enhanced strength stent analogous to that shown in FIG. 1. Enhanced strength stent 10 comprises a first end 12, a second end 14, and an expandable framework 16 disposed about a longitudinal axis A of the stent that defines a lumen 18 therethrough. The expandable framework 16 is expandable from a contracted state to the expanded state shown in FIG. 1. The expandable framework 16 has an outer surface 20 and an inner surface 22. In at least one embodiment, the outer surface 20 is the abluminal surface of the enhanced strength stent, and the inner surface 22 is the luminal surface of the enhanced strength stent. The expandable framework 16 has a thickness between the outer surface 20 and the inner surface 22.

The expandable framework 16 defines a plurality of openings 24. Each opening 24 has a perimeter defined by radial surfaces (or side walls) 28 of the expandable framework. Each radial surface 28 extends between the outer surface 20 and the inner surface 22. In various embodiments, the stent comprises a fiber-reinforced composite region, which will be described in further detail below. The fiber-reinforced composite region provides enhanced radial strength and stiffness for the expandable framework.

Figure 2:
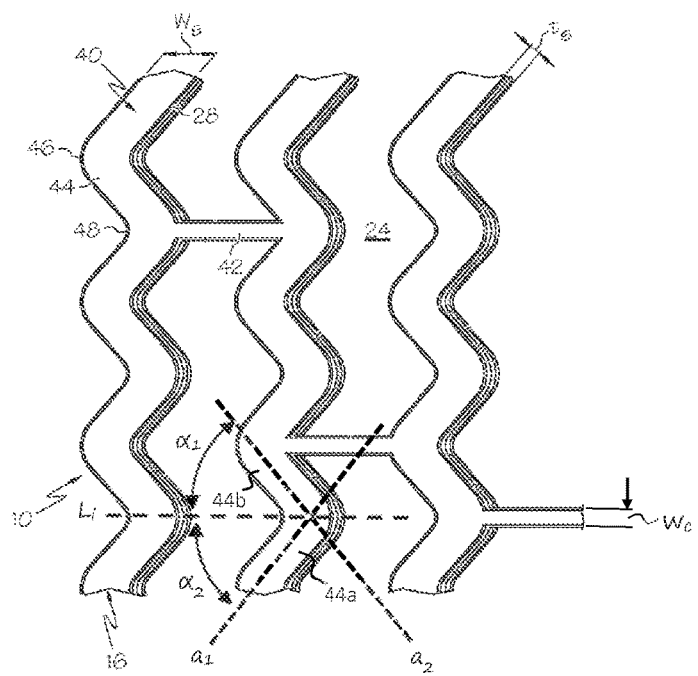
FIG. 2 is a schematic illustration of a portion of an enhanced strength polymer stent analogous to that of FIG. 1.

While the expandable framework 16 can have essentially any configuration, in some embodiments (such as shown in FIGS. 1 and 2), the expandable framework 16 comprises a plurality of axially spaced circumferential bands 40. In at least one embodiment, each circumferential band 40 is connected to an axially adjacent circumferential band 40 by a connector 42. In at least the embodiment shown, each circumferential band 40 has a zig-zag configuration comprising a plurality of strut segments 44 forming a plurality of alternating peaks 46 and troughs 48. In at least the embodiment shown in FIGS. 1 & 2, strut segments 44 and connectors 42 define openings 24. The strut segments 44 of the expandable framework 16 each have a width $W_s$ (measured perpendicular to the angled portion of the strut segment) and a thickness $t_s$, where the thickness $t_s$ is defined as the distance between the outer surface 20 and the inner surface 22 of the expandable framework 16. The connectors 42 of the expandable framework 16 each have a width $W_e$ and a thickness $t_s$.

As shown in FIG. 2, some strut segments 44a have an axis $a_1$ with a positive angle $\alpha_1$ (approximately 50°) relative to an imaginary line $L_i$ lying at a surface of the expandable framework 16 that is parallel to the longitudinal axis A of the framework, and other strut segments 44b have an axis $a_2$ with a negative angle $\alpha_2$ (approximately −50°) with regard to the imaginary line $L_i$. In other embodiments, the circumferential band 40 can be formed of strut segments 44 with other configurations. Moreover, the connectors 42 can have other configurations. Moreover, strut segments in accordance with the present disclose may have a wide range of angles other than the +/−50° shown, in either a crimped or an expanded state.

In accordance with various aspects of the present disclosure, a fiber welding process commonly called hot compaction is used to from a fiber-reinforced composite region comprising a binding polymer portion and a fibrous polymer reinforcement portion, which is oriented in one or multiple directions (e.g., oriented along the axes of stent strut segments, as discussed further below). In embodiments where the binding polymer portion surrounds the fibers of the fibrous polymer reinforcement portion, the binding polymer portion may be referred to herein as a matrix polymer or matrix polymer portion.

The hot compaction process has been used to make various three dimensional structures, has enabled a high level of control over mechanical properties, and results in increased elongation, strength, and modulus. See, e.g., K. P. Matabola et al., *J Mater Sci* (2009) 44:6213-6222. Hot compaction has been demonstrated for polylactic acid where it gave improved tensile strength and Young's modulus (i.e. toughness/ductility) (Li R, Yao D (2008) *J Appl Polym Sci*

107:2909). It has also proven effective for multiple other semicrystalline polymers, including polyethylene terephthalate, where impact strength (resistance to cracking) was improved 5-7 fold over standard samples (Rojanapitayakom P, Mather P T, Goldberg A J, Weiss R A (2005) *Polymer* 46:761). Biomaterials have been prepared from poly(methyl methacrylate), showing improvements in flexural and tensile strength, with concomitant improvement in fracture toughness and fatigue (Alcock B, Cabrera N O, Barkoula N M, Loos J, Peijs T (2007) *J Appl Polym Sci* 104:118; Mead W T, Porter R S (1978) *Appl Polym Sci* 22:3249). Other polymers processed using this method include polyethylene, polypropylene, and nylon 6,6 among others.

The processes presently employed by various stent manufacturers feature an attempt to control orientation, the ratio of crystalline to amorphous regions and crystal size, beginning with non-oriented, molten polymer. For example, one approach combines drawing and annealing a tube to achieve longitudinal crystalline orientation, followed by thermal expansion to achieve a degree of radial orientation. Another approach employed is based on a multilayer dip coating process to deposit layers of polymers with low or no alignment and minimal crystallinity. The resulting tubes are then post-processed in an attempt to achieve a degree of radial and longitudinal alignment.

In the present disclosure, on the other hand, a process is described which begins with oriented fibers, which can have very high modulus and strength. Such fibers may be formed by methods known in the art. For example, polymeric fibers for the practice of the present disclosure may be made by any suitable fiber forming technique, including, for example, melt spinning and solvent spinning (e.g., dry spinning and wet spinning). These processes typically employ extrusion nozzles having one or more orifices, also called distributors, jets or spinnerets. Fibers having a variety of cross-sectional shapes may be formed, depending upon the shape of the orifice(s). Some examples of fiber cross-sections include circular, oval, multi-lobed, polygonal (e.g., triangular, rectangular, hexagonal, etc.) and annular (hollow) cross-sections, among others. In melt spinning, polymers are heated to melt temperature prior to extrusion. In wet and dry spinning polymers are dissolved in a solvent prior to extrusion. In dry spinning, the extrudate is subjected to conditions whereby the solvent is evaporated, for example, by exposure to a vacuum or heated atmosphere (e.g., air) which removes the solvent by evaporation. In wet spinning the spinneret is immersed in a liquid, and as the extrudate emerges into the liquid, it solidifies. In either melt spinning or solvent spinning, the resulting fiber is typically taken up on a rotating mandrel or another take-up device. In various embodiments of the present disclosure, oriented fibers are formed by stretching (i.e., drawing) the fiber during take up to orient the polymer molecules. The degree of orientation in a given sample may be quantified, for example, using the Herman's orientation function (f), which is well known in the art, measured from the azimuthal scan of wide-angle x-ray diffraction pattern for the fiber or stent strut in question. See, e.g., P. Rojanapitayakorn et al., *Polymer* 46 (2005) 761-773, B. A. G. Schrauwen, et al., *Macromolecules* 2004, 37, 8618-8633 and Y. S. Wong, et al., *Acta Materialia* 56 (2008) 5083-5090. In certain preferred embodiments, the value of Herman's orientation function (f) ranges between 0.25 and 0.9, for example, ranging from 0.25 to 0.30 to 0.40 to 0.50 to 0.60 to 0.70 to 0.80 to 0.90, beneficially ranging from 0.5 to 0.9 in some embodiments, among other ranges.

Fibers for use in conjunction with the present disclosure may vary in width, for example, ranging from 10 nm to 1 mm in width, among other values, for example, ranging from 10 nm to 100 nm to 250 nm to 500 nm to 1 µm to 2.5 µm to 5 µm to 10 µm to 25 µm to 50 µm to 100 µm to 250 µm to 500 µm to 1000 µm. In certain beneficial embodiments, the fibers may range, for example, from 1 µm to 250 µm in width, for example, from 10 µm to 100 µm in width, among other ranges.

In certain embodiments, the fibers are oriented amorphous fibers. In certain embodiments, the fibers are oriented crystalline fibers. For example, the degree of crystallinity may range between 0% and 90%, for example, ranging from 0% to 10% to 20% to 30% to 40% to 50% to 60% to 70% to 80% to 90%, for instance, beneficially ranging from 50% and 90% in certain embodiments, among other ranges, which can be measured by suitable technique such as differential scanning calorimetry (DSC), as is well known in the art. See, e.g., P. Rojanapitayakorn et al., *Polymer* 46 (2005) 761-773. See also the primary method described in ASTM F2625, which was developed for ultra-high-molecular weight polyethylene, and which is also applicable to other polymers including polylactide homopolymers and copolymers, as referred to in ASTM F1925, developed for characterization of poly(L-lactide) or poly(D-lactide) homopolymers as well as L-lactide copolymerized with other bioabsorbable monomers.

In various embodiments, hot compaction of oriented fibers is used to create a polymer tube with tunable crystalline orientation. Uniquely, such fibers may be consolidated via a process that yields a hot compacted article with properties approaching those of the fibers used to form the article. In the present disclosure, hot compaction is employed to provide stents and other expandable devices with one or more of the following properties relative to presently available polymeric stents: improved crack resistance, improved tear resistance, thinner struts, and lower recoil, while maintaining the required strength.

In various embodiments, the degree of crystallinity may be measured using DSC, preferably in conjunction with a first heating scan following compaction as is known in the art. See, e.g., P. Rojanapitayakorn et al., *Polymer* 46 (2005) 761-773.

In various embodiments, self-reinforced composite regions are formed by first placing fibers in a suitable configuration using filament-winding, a process that is currently used to make pressure vessels, among other applications.

Filament winding involves winding fibers under varying amounts of tension over a male mold or mandrel. The mandrel typically has a circular cross-section, although a variety of other cross-sections are possible including oval and polygonal (e.g., triangular, rectangular, pentagonal, hexagonal, octagonal, etc.) configurations. The mandrel may be, for example, a steel or aluminum cylinder that has a carefully machined outer diameter with a precision ground and polished surface to ease of extraction of the mandrel, when desired. The mandrel rotates while a carriage moves parallel to the mandrel axis, laying down one or more fibers in the desired pattern. This process may be completely automated and controlled by specifically designed computer winding programs which ensure that the fiber is applied accurately in regards to fiber orientation and fiber density for the specific application. In addition to mandrel rotation and carriage velocity, the tension on the fiber(s) can be controlled, as it can have an effect on fiber volume fraction and void content. Applying fibers with higher tension may result in a final product with higher rigidity and strength, whereas lower tension may result in more flexibility. The orientation of the fibers can also be carefully controlled so that successive layers are plied or oriented differently from the previous layer. The angle at which the fiber is laid down will determine the properties of the final product.

Figure 3:
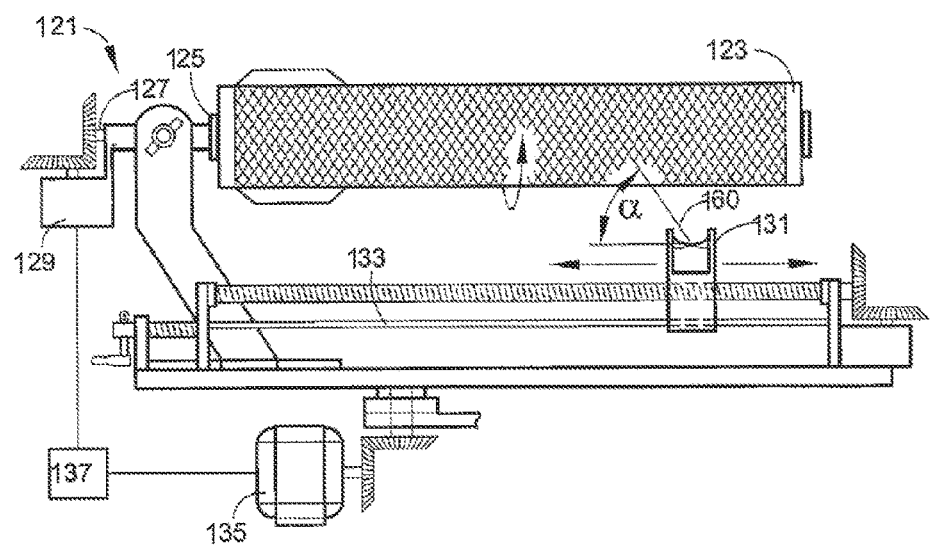
FIG. 3 is a schematic illustration of an apparatus employed in the formation of an enhanced strength polymer stent in accordance with an embodiment of the present disclosure.

One type of winding machine is shown schematically in FIG. 3 which very generally shows an apparatus that includes a cylindrical mandrel 123 which is mounted for revolution about its axis. Although not illustrated schematically, it is common that one end of the mandrel 123 is supported in a spindle while the other is secured to a suitable chuck 125 which connects to a drive shaft 127 that is rotated by a suitable drive motor 129. A portion of the machine frame supports a carriage 131 which reciprocates back and forth along one or more rails 133 that extend along the entire length of the mandrel 123, and typically for a short distance beyond either end. The rotation of the mandrel 123 in combination with the reciprocation of the carriage 131 allows the fibers to be wrapped around the mandrel in a helical fashion. The carriage 131 may be driven by a motor 135, and may be automated via a control system 137 that is capable of accepting a complex set of instructions to program the entire winding of fiber structure in a continuous manner.

The winding equipment may deposit a single fiber 160 from a single spool or multiple fibers from multiple spools. For example, as discussed below, combinations of different fibers (e.g., fibers of differing crystallinity, melting point, monomer composition, etc.) may be employed. In such embodiments, the relative linear densities (mass/length) of each fiber being unspooled may translate to varying compositions in the final product.

Each of the one or more spools may be equipped with a tension control device which maintains a desired tension on each individual fiber that is being wrapped about the rotating mandrel. In some embodiments, multiple strands may be drawn from respective spools and an array of these strands passed through a comb, which maintains the strands laterally separated from one another, such that the strands emerge as a flat band of parallel strands. By employing a pivotable comb, the width of the band may be varied. In another approach, width of the band may be set by a concave roller carried by the carriage 131 that delivers the strands of fibers to the mandrel 123 about which the band is being wound.

The winding machine shown in FIG. 3 has two axes of motion associated with the mandrel rotation and the carriage travel (typically horizontal). Two axis machines are well suited to the manufacture of cylindrical objects. In other embodiments, more complex machines may be used for fiber winding, such as four axis winding machines which may additionally have a radial (cross-feed) axis perpendicular to carriage travel and a rotating payout head mounted to the cross-feed axis. Machines with more than four axes can be used for complex applications, including six-axis winding machines, which typically have 3 linear and 3 rotation axes. Computer controlled filament winding machines typically employ software to generate machine paths and winding patterns as desired.

Turning again to FIG. 3, the winding angle $\alpha$ of the fiber(s) is determined by the linear velocity of the carriage relative to the rotational velocity of the mandrel and may vary between >0° and <90° (for example ranging from >0° to 5° to 10° to 15° to 20° to 25° 30° to 35° to 40° to 45° to 50° to 55° to 60° to 65° to 70° to 75° to 80° to 85° to <90°). For very low fiber angles (including 0°), fiber may be placed by hand. For a cylinder, low fiber angles are believed to provide good tensile strength, intermediate angles (~45°) are believed to provide good torsion strength, and high angles are believed to provide good hoop strength. An advantage of fiber winding is that different fiber angles can be laid down at different times to provide a structure with layers of fibers of varying orientation, with precise control over orientation, thus allowing the mechanical properties to be enhanced (e.g., in the direction of orientation).

For example, a first layer could be laid down at a particular angle relative to the longitudinal axis, followed by a subsequent layer with a different angle, with the process being repeated to build up a laminated structure that is later compacted to a monolithic, yet highly oriented structure.

For example, by making the angle $\alpha$ approximately 50° in FIG. 3, as the carriage 131 reciprocates back and forth, alternating fiber layers can be formed, approximately half of which (excluding edge effects at the point of carriage direction reversal) will have a fiber angle of approximately 50° relative to an imaginary line lying at a surface of the mandrel 123 that is parallel to the longitudinal axis of the mandrel 123 and approximately half of which will have a fiber angle of approximately −50° relative to an imaginary line lying at a surface of the mandrel 123 that is parallel to the longitudinal axis of the mandrel 123.

A fiber-reinforced composite structure formed in this way may provide enhanced mechanical properties to a stent formed from the fiber-reinforced composite structure, such as that shown in FIG. 2, wherein a first portion of the strut segments 44a have an angle of approximately 50° and second portion of the struts 44b have an angle of approximately −50°, relative to the imaginary line lying at a surface of the expandable framework that is parallel to the longitudinal axis of the framework. In this way, a structure may ultimately be formed, which comprises a composite region comprising a binding polymer portion and an oriented fibrous polymer reinforcement portion, wherein the oriented fibrous polymer reinforcement portion comprises (a) a first fraction (e.g., approximately 50%) of the oriented fibrous polymer reinforcement portion oriented at a first angle (i.e., approximately 50°) relative to the imaginary line, wherein the stent struts comprise first strut segments aligned with the first fraction and (b) a second fraction (e.g., approximately 50%) of the oriented fibrous polymer reinforcement portion oriented at a second angle (i.e., approximately −50°) relative to the imaginary line, wherein the stent struts comprise second strut segments aligned with the second fraction.

In various embodiments, the fibers are consolidated by the application of precise heat and pressure. In some embodiments, the heat and pressure may be applied by pressing a heated roller against the fibers on the mandrel, either during fiber winding or after fiber winding is complete. In other embodiments, the fibers may be compressed using a suitable mechanism (e.g., crimping, wrapping a polymer film around the fibers under tension, application of shrink wrap, etc.) followed by application of heat.

Heat may be applied, for example, by placing the compressed fibers in an oven. In this regard, computer-controlled ovens are available in which specific heating and cooling profiles are followed to consolidate the fibers.

Heat may also be applied, for example, by the apparatus used to compress the fibers. In a specific embodiment, the fibers may be compressed and heated by positioning an assembly including the mandrel and wound fibers within a crimping apparatus like that described in U.S. Pat. No. 8,042,251. The apparatus may include a crimping section having a number of crimping elements (e.g., movable blades) radially disposed about a central crimping lumen within which the assembly may be placed. When contracted, each of the crimping elements can be configured to provide an inwardly directed radial force to the inserted assembly in the crimping lumen. Heating may be performed by passing heating fluid through the mandrel, the crimping elements, or both. Similarly, cooling may be performed by passing cooling fluid through the mandrel, the crimping elements, or both. In this way heat and pressure may be precisely controlled as desired.

After the fibers have been consolidated, the resulting tubular fiber-reinforced composite can be further processed into the form of an expandable framework. In certain embodiments, the winding pattern executed is such that the tubular fiber-reinforced composite is in the form of a solid tube that is cut using any suitable cutting technique known in the polymer stent art, including mechanical cutting and laser cutting. For example, the tubular fiber-reinforced composite may be cut to form windows and stent elements like those shown in FIGS. 1-2. As indicated above, fibers forming the tubular fiber-reinforced composite may include edge effects at the positions where the carriage direction is reversed, which can be eliminated by cutting these portions away from the remainder of the structure. In certain other embodiments, the winding pattern executed is such that windows and stent elements are formed without the need for cutting.

Using the above and other techniques, stent bodies comprising fiber-reinforced composite region may be made from oriented fibers formed from a variety of polymers, which may be, for example, biodegradable or biostable, crystalline or amorphous, elastomeric or non-elastomeric, In various embodiments, the fibers include at least one polymer that has a glass transition temperature above room temperature (and preferably above human body temperature), a melting point above room temperature (and preferably above human body temperature), or both a melting point and a glass transition temperature above room temperature (and preferably above human body temperature), in order to provide suitable mechanical characteristics.

Examples of biodegradable polymers for use in the present disclosure may be selected from suitable members of the following, among many others: (a) polyester homopolymers and copolymers such as polyglycolide, poly-L-lactide, poly-D-lactide, poly-D,L-lactide, poly(beta-hydroxybutyrate), poly-D-gluconate, poly-L-gluconate, poly-D,L-gluconate, poly(epsilon-caprolactone), poly(delta-valerolactone), poly (p-dioxanone), poly(trimethylene carbonate), poly(lactide-co-glycolide) (PLGA), poly(lactide-co-delta-valerolactone), poly(lactide-co-epsilon-caprolactone), poly(lactide-co-beta-malic acid), poly(lactide-co-trimethylene carbonate), poly (glycolide-co-trimethylene carbonate), poly(beta-hydroxybutyrate-co-beta-hydroxyvalerate), poly[1,3-bis(p-carboxyphenoxy)propane-co-sebacic acid], and poly(sebacic acid-co-fumaric acid), among others, (b) poly(ortho ester) homopolymers and copolymers such as those synthesized by copolymerization of various diketene acetals and diols, among others, (c) polyanhydride homopolymers and copolymers such as poly(adipic anhydride), poly(suberic anhydride), poly(sebacic anhydride), poly(dodecanedioic anhydride), poly(maleic anhydride), poly[1,3-bis(p-carboxyphenoxy)methane anhydride], and poly[alpha,omega-bis(p-carboxyphenoxy)alkane anhydrides] such as poly[1,3-bis(p-carboxyphenoxy)propane anhydride] and poly[1,3-bis (p-carboxyphenoxy)hexane anhydride], among others; and (d) amino-acid-based homopolymers and copolymers including tyrosine-based polyarylates (e.g., copolymers of a diphenol and a diacid linked by ester bonds, with diphenols selected, for instance, from ethyl, butyl, hexyl, octyl and bezyl esters of desaminotyrosyl-tyrosine and diacids selected, for instance, from succinic, glutaric, adipic, suberic and sebacic acid), tyrosine-based polycarbonates (e.g., copolymers formed by the condensation polymerization of phosgene and a diphenol selected, for instance, from ethyl, butyl, hexyl, octyl and bezyl esters of desaminotyrosyl-tyrosine), and tyrosine-, leucine- and lysine-based polyesteramides; specific examples of tyrosine-based polymers include includes polymers that are comprised of a combination of desaminotyrosyl tyrosine hexyl ester, desaminotyrosyl tyrosine, and various di-acids, for example, succinic acid and adipic acid, among others.

Examples of biostable polymers for use in the present disclosure may be selected from suitable members of the following, among many others: (a) homopolymers and copolymers consisting of or containing one or more acrylic acid monomers such as the following: acrylic acid and its salt forms (e.g., potassium acrylate and sodium acrylate); acrylic acid anhydride; acrylic acid esters including alkyl acrylates (e.g., methyl acrylate, ethyl acrylate, propyl acrylate, isopropyl acrylate, butyl acrylate, sec-butyl acrylate, isobutyl acrylate, tert-butyl acrylate, hexyl acrylate, cyclohexyl acrylate, isobornyl acrylate, 2-ethylhexyl acrylate, dodecyl acrylate and hexadecyl acrylate), arylalkyl acrylates (e.g., benzyl acrylate), alkoxyalkyl acrylates (e.g., 2-ethoxyethyl acrylate and 2-methoxyethyl acrylate), halo-alkyl acrylates (e.g., 2,2,2-trifluoroethyl acrylate) and cyano-alkyl acrylates (e.g., 2-cyanoethyl acrylate); acrylic acid amides (e.g., acrylamide, N-isopropylacrylamide and N,N dimethylacrylamide); and other acrylic-acid derivatives (e.g., acrylonitrile); (b) homopolymers and copolymers consisting of or containing one or more methacrylic acid based monomers such as the following: methacrylic acid and its salts (e.g., sodium methacrylate); methacrylic acid anhydride; methacrylic acid esters (methacrylates) including alkyl methacrylates (e.g., methyl methacrylate, ethyl methacrylate, isopropyl methacrylate, butyl methacrylate, isobutyl methacrylate, t-butyl methacrylate, hexyl methacrylate, cyclohexyl methacrylate, 2-ethylhexyl methacrylate, octyl methacrylate, dodecyl methacrylate, hexadecyl methacrylate, octadecyl methacrylate, aromatic methacrylates (e.g., phenyl methacrylate and benzyl methacrylate), hydroxyalkyl methacrylates (e.g., 2-hydroxyethyl methacrylate and 2-hydroxypropyl methacrylate), aminoalkyl methacrylates (e.g., diethylaminoethyl methacrylate and 2-tert-butyl-aminoethyl methacrylate), additional methacrylates (e.g., isobornyl methacrylate and trimethylsilyl methacrylate); and other methacrylic-acid derivatives (e.g., methacrylonitrile); (c) homopolymers and copolymers consisting of or containing one or more vinyl aromatic monomers (i.e., those having aromatic and vinyl moieties) such as the following: unsubstituted vinyl aromatics (e.g., styrene and 2-vinyl naphthalene); vinyl substituted aromatics (e.g., α-methyl styrene); and ring-substituted vinyl aromatics including ring-alkylated vinyl aromatics (e.g., 3-methylstyrene, 4-methylstyrene, 2,4-dimethylstyrene, 2,5-dimethylstyrene, 3,5-dimethylstyrene, 2,4,6-trimethylstyrene, and 4-tert-butylstyrene), ring-alkoxylated vinyl aromatics (e.g., 4-methoxystyrene and 4-ethoxystyrene), ring-halogenated vinyl aromatics (e.g., 2-chlorostyrene, 3-chlorostyrene, 4-chlorostyrene, 2,6-dichlorostyrene, 4-bromostyrene and 4-fluorostyrene) and ring-ester-substituted vinyl aromatics (e.g., 4-acetoxystyrene); (d) homopolymers and copolymers consisting of or containing one or more vinyl monomers (beyond the above vinyl aromatic monomers) such as the following: vinyl alcohol; vinyl esters (e.g., vinyl benzoate, vinyl 4-tert-butyl benzoate, vinyl cyclohexanoate, vinyl pivalate, vinyl trifluoroacetate and vinyl butyral); vinyl amines (e.g., 2-vinyl pyridine, 4-vinyl pyridine, and vinyl carbazole); vinyl halides (e.g., vinyl chloride and vinyl fluoride); alkyl vinyl ethers (e.g., methyl vinyl ether, ethyl vinyl ether, propyl vinyl ether, butyl vinyl ether, isobutyl vinyl ether, 2-ethylhexyl vinyl ether, dodecyl vinyl ether, tert-butyl vinyl ether and cyclohexyl vinyl ether); and other vinyl compounds (e.g., 1-vinyl-2-pyrrolidone and vinyl ferrocene); (e) homopolymers and copolymers consisting of or containing one or more aromatic monomers (beyond the above vinyl aromatic monomers) such as acenaphthalene and indene; (f) homopolymers and copolymers consisting of or containing one or more cyclic ether monomers such as the following: tetrahydrofuran, trimethylene oxide, methyl glycidyl ether, butyl glycidyl ether, allyl glycidyl ether, epibromohydrin, epichlorohydrin, 1,2-epoxybutane, 1,2-epoxyoctane and 1,2-epoxydecane; (g) homopolymers and copolymers consisting of or containing one or more ester monomers (beyond those ester monomers listed above) such as ethylene malonate, vinyl acetate and vinyl propionate; (h) homopolymers and copolymers consisting of or containing one or more alkene monomers such as the following: unsubstituted alkene monomers (e.g., ethylene, propylene, isobutylene, 1-butene, trans-butadiene, 4-methyl pentene, 1-octene, 1-octadecene, and other α-olefins, as well as cis-iprene and trans-isoprene) and halogenated alkene monomers (e.g., vinylidene chloride, vinylidene fluoride, cis-chlorobutadiene, trans-chlorobutadiene, and tetrafluoroethylene); (i) homopolymers and copolymers consisting of or containing one or more organo-siloxane monomers such as dimethylsiloxane, diethylsiloxane, methylethylsiloxane, methylphenylsiloxane and diphenylsiloxane; and (j) various other polymers including polyurethanes, polyureas, polyamides including nylons, polycarbonates, polyesters, poly(ether ketone) (PEEK), and poly(arylene ether ketone) PAEK.

As previously indicated, the present disclosure provides an expandable medical device comprising an expandable framework that comprises a composite region is provided. In various embodiments, the composite region comprises a binding polymer portion and an oriented fibrous polymer reinforcement portion. The expandable medical device may be, for example, a stent, among other possibilities.

In certain embodiments, the composite region is provided from one or more oriented fibers that comprise the same polymer composition. In these embodiments, heat and pressure are carefully applied such that the one or more fibers partially melt and the binding polymer portion is formed from a melted outer surface portion of the fibers, whereas the oriented fibrous polymer reinforcement portion is formed from residual core regions of the one or more polymer fibers, which are not melted. In embodiments where the binding polymer portion surrounds the residual core regions, the binding polymer portion may be referred herein to as a matrix polymer or matrix polymer portion. In certain embodiments, the surface portion of each fiber is melted under a comparatively low contact pressure, after which a substantially higher pressure is applied for a short time to achieve enhanced consolidation of the structure. Such a structure maintains the properties of the fibers forming the composite region to a significant degree. Moreover, the resulting structure has enhanced mechanical properties, with excellent interfacial adhesion, due to the identical chemistry of the binding polymer portion and the oriented fibrous polymer reinforcement portion.

In a specific embodiment, the fibers used to form the composite region contain polylactide (also referred to as polylactic acid) as the polymeric component. In certain embodiments, chiral polylactides, specifically poly(l-lactide) (also referred to as poly(l-lactic acid)) or poly(d-lactide) (also referred to as poly(d-lactic acid)), are employed, because oriented fibers can be formed from such polymers that have a relatively high degree of crystallinity. For example, the degree of crystallinity may range between 50% and 90% which can be measured by suitable technique such as DSC.

In this regard, while both oriented amorphous and oriented crystalline polymer fibers (e.g., crystalline fibers having a crystallinity ranging from 10% to 90%) may be employed herein, the crystalline polymers are particularly beneficial in certain embodiments, due to the fact that they have intrinsically higher mechanical properties in original fiber form and because melted material can recrystallize after heating and compression. Without be bound by theory, it is believed that upon application of pressure an heat, surfaces of the crystalline fibers melt, allowing molecular diffusion of polymers from each fiber which entangle and which crystallize as the resulting composite structure cools.

In certain embodiments, the binding polymer portion of the composite region is formed from a first polymer and the oriented fibrous polymer reinforcement portion is formed from a second polymer that is different from the first polymer (e.g., differing in melting point, in crystallinity, in monomer composition, etc.).

In some of these embodiments, the composite region may be formed by compressing and heating one or more polymer fibers, which comprise an oriented polymer core formed from the second polymer and a polymer coating formed from the first polymer, to a temperature that is sufficiently elevated to cause the first polymer in the polymer coating to flow and form the binding polymer portion, but which is not sufficient to cause substantial flow of the second polymer, thereby retaining the oriented fibrous nature of the polymer core, which corresponds to the oriented fibrous polymer reinforcement portion of the composite. In embodiments where the binding polymer portion surrounds the core of second polymer, the binding polymer portion may be referred herein to as a matrix polymer or matrix polymer portion.

In other of these embodiments, the composite region may be formed by compressing and heating one or more first polymer fibers formed from the first polymer and one or more second oriented polymer fibers formed from the second polymer to a temperature that is sufficiently elevated to cause the first polymer in the first polymer fiber to flow and form the binding polymer portion, but which is not sufficient to cause substantial flow of the second polymer in the second polymer fibers, such that the second polymer fibers form the oriented fibrous polymer reinforcement portion of the composite. In embodiments where the binding polymer portion surrounds the second polymer fibers, the binding polymer portion may be referred herein to as a matrix polymer or matrix polymer portion.

In certain embodiments, the first polymer is a biodegradable polymer and the second polymer is a biostable polymer. In this case the binding polymer portion of the composite region will be formed from a biodegradable polymer and the fibrous polymer reinforcement portion is formed from a biostable polymer. This results in a medical device which ultimately decreases in mass in vivo, but leaves a structure behind to continue to perform a long-term function.

In certain embodiments, the first polymer is a low melting point grade of a given polymer and the second polymer is a high melting point grade of the same polymer. For example, one or more polymer fibers may be heated and compressed that have a core of oriented higher melting point grade PLA (e.g., higher molecular weight PLA) surrounded by a layer of lower melting point grade PLA (e.g., lower molecular weight PLA). As another example, one or more first polymer fibers formed from lower melting point grade PLA (e.g., lower molecular weight PLA) and one or more second oriented polymer fibers formed from higher melting point grade PLA (e.g., higher molecular weight PLA) may be heated and compressed.

In certain embodiments, the first polymer is an amorphous form of a given polymer and the second polymer is a crystalline form of the same polymer. For example, one or more polymer fibers may be heated and compressed which have a core of oriented crystalline PLA (e.g., chiral PLA) surrounded by a layer amorphous PLA (e.g., racemic PLA). As another example, one or more first polymer fibers formed from amorphous PLA and one or more second oriented polymer fibers formed from crystalline PLA are heated and compressed. During processing, the fibers may be compressed and heated to a temperature that is below the $T_m$ of the crystalline PLA and sufficiently above the $T_g$ of the amorphous PLA such that the amorphous PLA becomes rubbery and sticky and fuses together through chain diffusion at the fiber interfaces under compression.

In certain embodiments, the first and second polymers may comprise differing monomeric constituents.

For example, in some embodiments, the first polymer comprises an amorphous or substantially amorphous polymer (e.g., having a crystallinity of less than 25%) and the second polymer comprises a substantially crystalline polymer (e.g., having a crystallinity of at least 40%). One potential advantage of such embodiments, is that a resultant device with increased toughness or fatigue resistance, since amorphous regions are better able to absorb energy and yield without cracking.

In some embodiments, the first polymer may be poly (lactide-co-glycolide) (PLGA) and the second polymer may be racemic or chiral polylactide, preferably chiral polylactide, more preferably poly(l-lactide).

Where copolymers such as PLGA are employed, copolymers with a variety of monomer ratios, and thus a range of properties, may be available or synthesized. For example, where PLGA is used, a variety of lactide:glycolide molar ratios will find use herein, with the ratio depending, for example, on the rate of degradation desired. Lactide:glycolide ratios may range, for example from 50:50 to 98:2. In this regard, a 50:50 PLGA polymer, containing 50% d,l-lactide and 50% glycolide, will provide a fast resorbing copolymer, while 75:25 PLGA degrades more slowly, and 85:15 PLGA, 90:10 PLGA, 95:5 PLGA and 98:2 PLGA degrade progressively more slowly, due to the increased lactide component. Mixtures of fibers with varying lactide:glycolide ratios may also find use herein in order to achieve desired release kinetics for drugs found within the fibers as discussed further below. Degradation rate may also be controlled by such factors as polymer molecular weight and polymer crystallinity. If desired crystallinity can be virtually eliminated by using racemic d,l-lactide in the copolymer. Crystallinity may also be incrementally increased by increasing the amount of lactide in a PLGA formed using chiral l-lactide (or d-lactide). For example, a 50:50 PLGA polymer, containing 50% l-lactide and 50% glycolide, will provide a lower crystallinity copolymer, while 75:25 PLGA has higher crystallinity, and 85:15 PLGA, 90:10 PLGA, 95:5 PLGA and 98:2 PLGA have progressively higher crystallinity still.

One advantage of forming a fiber-reinforced composite region comprising a PLGA binding polymer portion and a PLA oriented fibrous polymer reinforcement portion, using various processing methods and structural components as described herein, is that a stent may be provided that degrades more rapidly than a stent made from pure PLA, while providing the strength inherent in pure PLA fibers. In addition, since the PLGA can be selected with differing amounts of crystallinity, or even with no crystallinity, the resultant stent is expected to have increased toughness or fatigue resistance, since amorphous regions are better able to absorb energy and yield without cracking. More generally, the approach allows composition tailoring that would enable tuning of both mechanical properties and degradation rates.

In this regard, one may make biodegradable stents or biostable stents using a combination of (a) a more crystalline polymer (e.g., ranging from 35 to 90 wt % of the more crystalline polymer), such as poly(L-lactic acid) (PLLA) (also referred to as poly-L-lactide), a crystalline polyisobutylene polyurethane or a poly(ether ketone), with (b) a less crystalline or completely amorphous polymer (e.g., ranging from 10 to 65 wt % of the less crystalline or completely amorphous polymer), such as poly(lactic-acid-co-glycolic acid) (PLGA) (also referred to as poly(lactide-co-glycolide)), a less crystalline or completely amorphous polyisobutylene-polyurethane, or polymethylmethacrylate. An advantage of this process would be the ability to modify the mechanical properties and, in the case of biodegradable polymers, modify the degradation rate of the resultant device, while maintaining superior strength.

As a specific example, a stent may be formed from PLLA fibers coated with PLGA, may be formed from a mixture of PLLA fibers and PLGA fibers, or both. The PLGA (which forms the binding polymer portion) has a lower processing temperature, thereby allowing a composite to be formed with no significant change to the crystallinity of the PLLA fibers during processing (which form the oriented fibrous polymer reinforcement portion). The resulting structure would maintain the strength of the PLLA fibers. When implanted, the PLGA would degrade significantly more rapidly than the PLLA, so the stent would allow the vessel to approach its normal motion sooner than in the case of a PLLA-only stent. This is desirable for many applications. For example, a coronary stent made from PLLA typically maintains its mechanical integrity for more than 9 months, whereas the optimum healing time for the artery is 3-6 months. By selecting a PLGA with different ratios of the lactide and glycolide, the loss of mechanical properties may be tailored to occur anywhere between 2 months and 9 months.

In the case of PLGA and PLLA, a suitable compaction temperature may be above $T_g$ of PLGA (~50° C.) and below $T_m$ of PLLA (~155° C.), yielding PLA fibers bonded together by PLGA. Using such a process may allow a stent to be formed that combines the strength of highly crystalline PLLA and the ductility of amorphous PLGA, while achieving a tailorable degradation rate dependent on the PLGA ratio selected.

In a particular embodiment, PLGA coated PLLA fibers, a mixture of PLLA and PLGA fibers, or both, may be wound onto a mandrel and compacted with sufficient heat and pressure form a PLGA matrix with a fibrous PLLA reinforcement, yielding a consolidated, highly stiff structure. In the case of PLGA coated PLLA fibers, the PLGA coating may be formed on the PLLA fiber core in a coextrusion process or in a fiber coating process. Such a process has the potential to yield a stent combining the strength of highly crystalline PLLA and the increased degradation rate and ductility of amorphous or semi-amorphous PLGA. Since the PLGA can be selected with differing amounts of crystallinity, or even with no crystallinity, the resultant stent has the potential to increase toughness or fatigue resistance, since the amorphous regions are expected to absorb energy such as impact energy or the energy imparted due to compression resulting from a beating heart. Moreover, degradation properties may be tailored by varying (a) a ratio of PLLA to PLGA (for example, by varying coating thickness in the case of PLGA coated PLLA fibers or by varying a ratio of PLLA fibers to PLGA fibers in the case of fiber mixtures) and/or (b) a ratio of lactide to glycolide within the PLGA fibers. Each or both of these ratios may also be varied along the length of the stent if desired.

As previously indicated, winding parameters provide control over the pitch of molecular PLLA orientation relative to the mandrel axis. As elsewhere herein, the winding process may be executed to yield a solid tube, ready for cutting (e.g., laser-cutting) into an expandable stent, or the winding process itself may be executed to yield a pattern with struts and windows, such that stent windows and struts may be formed without laser cutting.

Expandable structures in accordance with the present disclosure may include additional agents including imaging agents and therapeutically effective agents.

Beneficial imaging agents include (a) contrast agents for use in connection with x-ray fluoroscopy, including metals (e.g., tungsten, platinum, gold, and others), metal salts and oxides (particularly bismuth and barium salts and oxides), and iodinated compounds, among others, (b) contrast agents for use in conjunction with ultrasound imaging, including inorganic and organic echogenic particles (i.e., particles that result in an increase in the reflected ultrasonic energy) or inorganic and organic echolucent particles (i.e., particles that result in a decrease in the reflected ultrasonic energy), and (c) contrast agents for use in conjunction with magnetic resonance imaging (MRI), including contrast agents that contain elements with relatively large magnetic moment such as Gd(III), Mn(II), Fe(III) and compounds (including chelates) containing the same, such as gadolinium ion chelated with diethylenetriaminepentaacetic acid.

Beneficial therapeutic agents include anti-thrombotic agents, anti-proliferative agents, anti-inflammatory agents, anti-migratory agents, agents affecting extracellular matrix production and organization, antineoplastic agents, antimitotic agents, anesthetic agents, anti-coagulants, vascular cell growth promoters, vascular cell growth inhibitors, cholesterol-lowering agents, vasodilating agents, agents that interfere with endogenous vasoactive mechanisms, antibiotics, and biologics, among others.

Specific agents include taxanes such as paclitaxel, olimus family drugs such as sirolimus, everolimus, biolimus and tacrolimus, Epo D, dexamethasone, estradiol, halofuginone, cilostazole, geldanamycin, ABT-578 (Abbott Laboratories), trapidil, liprostin, Actinomcin D, Resten-NG, Ap-17, abciximab, clopidogrel, Ridogrel, beta-blockers, bARKct inhibitors, phospholamban inhibitors, and Serca 2 gene/protein, resiquimod, imiquimod (as well as other imidazoquinoline immune response modifiers), human apolioproteins (e.g., AI, AII, AIII, AIV, AV, etc.), vascular endothelial growth factors (e.g., VEGF-2), rifampin, minocycline, and infliximab, as well as derivatives of the forgoing, among many others.

Numerous additional therapeutic agents useful for the practice of the present disclosure may be selected from those described in paragraphs [0089] to [0091] of U.S. Patent Application Pub. No. 2010/0233227 to Weber, the entire disclosure of which is hereby incorporated by reference.

Such additional agents may be included in all the polymer fibers used to form the device or just a portion of the fibers, which fibers can be positioned where desired during the winding process. For example, where a therapeutic agent is provided, it may only be included in the outermost layers which come into closest contact with a body lumen upon deployment. As another example, where multiple fibers are provided, each with differing degradation rates, the therapeutic agent can be included in the more rapidly degrading fiber for more rapid release, in the less rapidly degrading fiber for more extended release, or both. As yet another example, a first therapeutic agent may be included in the more rapidly degrading fiber for more rapid release and a second differing therapeutic agent (that differs from the first therapeutic agent) may be included in the less rapidly degrading fiber for more extended release.

Although various embodiments are specifically illustrated and described herein, it will be appreciated that modifications and variations of the present disclosure are covered by the above teachings and are within the purview of the appended claims without departing from the spirit and intended scope of the disclosure.

What is claimed is:

1. A medical device, comprising:
an expandable framework of oriented polymer fibers, wherein a binding polymer portion of one polymer fiber and a fibrous polymer reinforcement portion of another polymer fiber form a reinforced composite region, wherein the fibrous polymer reinforcement portion comprises, relative to a longitudinal axis of the framework, one of the following fractions, any two of the following fractions, or all three of the following fractions:
a first fraction oriented at a first angle relative to the longitudinal axis;
a second fraction oriented at a second angle relative to the longitudinal axis; and
a third fraction oriented at a third angle relative to the longitudinal axis.

2. The medical device of claim 1, wherein the binding polymer portion is in the form of a polymer matrix that surrounds the fibrous polymer reinforcement portion.

3. The medical device of claim 1, wherein the fibrous polymer reinforcement portion has a crystallinity of at least 45%.

4. The medical device of claim 1, wherein a value of a Herman's orientation function (f) for the composite region ranges between 0.25 and 0.9.

5. The medical device of claim 1, wherein the composite region is a self-reinforced composite region in which the binding polymer portion and the fibrous polymer reinforcement portion are formed from one or more oriented polymer fibers having the same composition.

6. The medical device of claim 1, wherein the binding polymer portion comprises a first polymer and the fibrous polymer reinforcement portion comprises a second polymer that is different than the first polymer.

7. The medical device of claim 6, (a) wherein the composite region is formed by compressing and heating one or more first polymer fibers formed from the first polymer and one or more second polymer fibers formed from the second polymer to melt only the first polymer or (b) wherein the composite region is formed by compressing and heating one or more polymer fibers that comprise a polymer core formed from the second polymer and a polymer coating formed from the first polymer to melt only the coating.

8. The medical device of claim 1, wherein the fibrous polymer reinforcement portion comprises polylactide.

9. The medical device of claim 1, wherein the fibrous polymer reinforcement portion comprises polylactide and the binding polymer portion comprises polylactide, or wherein the fibrous polymer reinforcement portion comprises polylactide and the binding polymer portion comprises poly(lactide-co-glycolide).

10. The medical device of claim 1, wherein the composite region is formed by a process that comprises heating and compressing one or more fibers that comprise an oriented polylactide core and a poly(lactide-co-glycolide) coating, or wherein the composite region is formed by a process that comprises heating and compressing a mixture of fibers that comprises polylactide fibers and poly(lactide-co-glycolide) fibers.

11. The medical device of claim 1, wherein the medical device is a stent and the expandable framework is a stent body, and wherein the stent body comprises a plurality of stent struts.

12. The medical device of claim 1, wherein the first angle ranges from 30° to 60° relative to the longitudinal axis, the second angle ranges from −30° to −60° relative to the longitudinal axis, and the third fraction ranges from 85° to 95° relative to the longitudinal axis.

13. The medical device of claim 11, wherein the stent struts comprise one of the following strut segments, any two of the following strut segments, or all three of the following strut segments: (a) first strut segments aligned with the first fraction, (b) second strut segments aligned with the second fraction, and (c) third strut segments aligned with the third fraction.

14. An assembly comprising a balloon and a stent disposed on the balloon, wherein the stent comprises an expandable body of oriented polymer fibers, the body having a longitudinal axis, wherein a binding polymer portion of one polymer fiber and a fibrous polymer reinforcement portion of another polymer fiber form a reinforced composite region, wherein upon expansion of the stent by the balloon, the fibrous polymer reinforcement portion comprises one of the following fractions, any two of the following fractions, or all three of the following fractions: (a) a first fraction of the fibrous polymer reinforcement portion oriented at a first angle ranging from 30° to 60° relative to an imaginary line lying at a surface of the stent body that is parallel to the longitudinal axis of the stent body, wherein the stent comprises first strut segments aligned with the first fraction, (b) a second fraction of the fibrous polymer reinforcement portion oriented at a second angle ranging from −30° to −60° relative to the imaginary line, wherein the stent comprises second strut segments aligned with the second fraction, and (c) a third fraction of the fibrous polymer reinforcement portion oriented at a third angle ranging from 85° to 95° relative to the imaginary line, and wherein the stent comprises third strut segments aligned with the third fraction.

* * * * *